United States Patent
Whitesell et al.

(10) Patent No.: US 11,129,431 B2
(45) Date of Patent: Sep. 28, 2021

(54) MAGNETIC GOGGLE ATTACHMENT

(71) Applicant: Bell Sports, Inc., Scotts Valley, CA (US)

(72) Inventors: Scott S. Whitesell, Boulder Creek, CA (US); Timothy E. Piver, Boulder Creek, CA (US)

(73) Assignee: Bell Sports, Inc., Scotts Valley, CA (US)

( * ) Notice: Subject to any disclaimer, the term of this patent is extended or adjusted under 35 U.S.C. 154(b) by 126 days.

(21) Appl. No.: 16/405,002

(22) Filed: May 7, 2019

(65) Prior Publication Data
US 2020/0352271 A1 Nov. 12, 2020

(51) Int. Cl.
*A42B 3/18* (2006.01)
*F16B 1/00* (2006.01)
*A44B 99/00* (2010.01)

(52) U.S. Cl.
CPC .............. *A42B 3/185* (2013.01); *A44B 99/00* (2013.01); *A44D 2203/00* (2013.01); *F16B 2001/0035* (2013.01); *Y10T 24/32* (2015.01)

(58) Field of Classification Search
CPC ............. Y10T 24/32; F16B 2001/0035; A44D 2203/00
See application file for complete search history.

(56) References Cited

U.S. PATENT DOCUMENTS

| | | | |
|---|---|---|---|
| 5,664,298 A * | 9/1997 | Nessar-Ivanovic | A44C 5/2071 24/303 |
| 6,598,271 B2 * | 7/2003 | Nire | A41F 1/002 24/265 WS |
| 6,857,169 B2 * | 2/2005 | Chung | A44B 11/258 24/303 |
| 9,936,772 B2 * | 4/2018 | Paik | A45F 3/047 |
| 10,085,521 B2 * | 10/2018 | Chen | A45C 13/1069 |
| 10,143,270 B2 * | 12/2018 | Fiedler | A44B 11/2588 |
| 2012/0180203 A1 | 7/2012 | Giroux et al. | |
| 2013/0185849 A1 | 7/2013 | Laughlin et al. | |
| 2018/0092427 A1 | 4/2018 | Jacobsen | |

FOREIGN PATENT DOCUMENTS

EP  3646829 A1  5/2020

OTHER PUBLICATIONS

Extended European Search Report cited in related European Application No. 20170698.3 dated Sep. 18, 2020.

* cited by examiner

*Primary Examiner* — Robert Sandy
(74) *Attorney, Agent, or Firm* — Walter M. Egbert, III; Gerard M. Donovan; Reed Smith LLP (57) ABSTRACT

A magnetic mechanical latching attachment for connecting goggles to a helmet includes a goggle attachment portion configured to mechanically and magnetically attach to a helmet attachment portion. The goggle attachment portion and helmet attachment portion include complimentary interlocking features that mechanically lock the portions together when attached and magnetic features that assist engagement of the complimentary interlocking features in a locked position. A related method of coupling goggles to a helmet, as well as a helmet-goggle attachment system, is provided.

7 Claims, 7 Drawing Sheets

MAGNETIC GOGGLE ATTACHMENT

TECHNICAL FIELD

Aspects of this document relate generally to goggles configured to be worn with a helmet, and more specifically to a magnetic mechanical latching attachment for connecting goggles to a helmet.

BACKGROUND

Protective headgear is used in outdoor sports to reduce the severity of participant head injuries. In some outdoor activities, it may advantageous to wear goggles to protect eyes from environmental conditions, such as dust, dirt, rocks, exhaust, wind, rain or snow, as well as bright sunshine or light. In such environments, participants wearing helmets often desire to also wear goggles. However, when goggles are worn at the same time as a helmet, it can be difficult to maintain a good, safe and secure fit of both the helmet and the goggles.

Conventionally, various structural configurations and techniques have been utilized in an attempt to secure goggles into a proper fit while wearing a helmet. Some attempts have simply involved wrapping an elastic securing strap of the goggles around a helmet exterior when both are worn. Yet the strap may tend to move on the helmet causing the fit of the goggles to become unsecured and improper. Other attempts have included provision of engagement features on the exterior of a helmet to help retain an elastic goggle strap in a proper position to maintain a secure fit. However, such exterior engagement features often make it difficult for a user to readily and efficiently put goggles on an off while wearing a helmet.

SUMMARY

Aspects of the disclosure relate to a magnetic mechanical latching attachment for connecting goggles to a helmet, the magnetic mechanical latching attachment comprising a goggle attachment portion having a mechanical latch member, the mechanical latch member including: a latch protrusion extending perpendicular to an axial length of the latch member, and at least one perpendicularly-oriented magnetic attractor, wherein the goggle attachment portion is configured to attach to goggles, a helmet attachment portion having a latch opening, the latch opening including, a latch protrusion extending perpendicular to an axial length of the latch opening, and at least one perpendicularly-oriented magnetic attractor, wherein the helmet attachment portion is configured to attach to a surface of a helmet, and wherein the latch member of the goggle attachment portion is configured to mate with the latch opening of the helmet attachment portion, and, when mated, the at least one perpendicularly-oriented magnetic attractor of the goggle attachment portion is located such that it is magnetically attracted to the at least one perpendicularly-oriented magnetic attractor of the helmet portion, wherein the magnetic attraction of the perpendicularly-oriented magnetic attractor of the goggle attachment portion to the perpendicularly-oriented magnetic attractor of the helmet portion facilitates a holding of the mechanical latch member of the goggle attachment portion in a locked position with respect to the latch opening of the helmet attachment portion in a manner wherein axial movement of the goggle attachment portion away from the helmet attachment portion is restricted by a mechanical interlock of the perpendicular protrusion of the latch member of the goggle attachment portion with the perpendicular protrusion of the latch opening of the helmet attachment portion.

Particular embodiments may comprise one or more of the following features. The helmet attachment portion may be located on an interior surface of the helmet. The at least one perpendicularly-oriented magnetic attractor of the goggle attachment portion, the at least one perpendicularly-oriented magnetic attractor of the helmet attachment portion, the at least one axially-oriented magnetic attractor of the goggle attachment portion, and the at least one axially-oriented magnetic attractor of the helmet attachment portion may all include magnets. The goggle attachment portion may further comprise at least one axially-oriented magnetic attractor and the helmet attachment portion further comprises at least one axially-oriented magnetic attractor. When the goggle attachment portion is mated with the helmet attachment portions, the at least one axially-oriented magnetic attractor of the goggle attachment portion may be located such that it is magnetically attracted to the at least one axially-oriented magnetic attractor of the helmet portion. The magnetic attraction between the axially-oriented magnetic attractor of the goggle attachment portion and the axially-oriented magnetic attractor of the helmet attachment portion tends the goggle attachment portion towards a mated condition with the helmet attachment portion. The goggle attachment portion may be configured to be securely and removably attached to goggles. The helmet attachment portion may be configured to be securely and removably attached to a surface of the helmet.

Aspects of the disclosure relate to a method of coupling goggles to a helmet comprising providing goggles having a latch member, providing a helmet having a latch opening positioned on an interior surface of the helmet, wherein the latch opening is configured to receive and removably latch to the latch member of the goggles, and coupling the goggles to the helmet by removably latching the latch member of the goggles to the latch opening located on the interior surface of the helmet.

Particular embodiments may comprise one or more of the following features. The goggles may have at least one magnetic attractor. The at least one magnetic attractor of the goggles may be perpendicularly-oriented with regard to an axial length of the latch member. The helmet may have at least one magnetic attractor. The at least one magnetic attractor of the helmet may be perpendicularly-oriented with regard to an axial length of the latch opening. The goggles may be coupled to the helmet, the at least one perpendicularly-oriented magnetic attractor of the goggles is located such that it is magnetically attracted to the at least one perpendicularly-oriented magnetic attractor of the helmet, wherein the magnetic attraction of the perpendicularly-oriented magnetic attractor of the goggles to the perpendicularly-oriented magnetic attractor of the helmet facilitates a holding of the latch member of the goggles in a locked position with respect to the latch opening of the helmet, in a manner wherein axial movement of the goggles away from the helmet is restricted by a mechanical interlock of a perpendicular protrusion of the latch member of the goggles with a perpendicular protrusion of the latch opening of the helmet.

Aspects of the disclosure relate to a helmet-goggle attachment system comprising goggles having an attachment portion, wherein the attachment portion includes a magnetic attractor, a helmet having an attachment portion located on an interior surface of the helmet and including a magnetic attractor, wherein the attachment portion of the helmet is configured to mechanically attach to the attachment portion of the goggles, and wherein the magnetic attractor of the attachment portion of the goggles is magnetically attracted to the magnetic attractor of the attachment portion of the helmet and the magnetic attraction presents a force that helps facilitate a mechanical interlock between the attachment portion of the goggles and the attachment portion of the helmet, when the goggles are attached to the interior surface of the helmet.

Particular embodiments may comprise one or more of the following features. The attachment portion of the goggles may include a latch member configured to be inserted into and mated with a latch opening of the attachment portion of the helmet. The latch member may include a protrusion extending perpendicular to an axial length of the latch member and the latch opening includes a protrusion extending perpendicular to an axial length of the latch opening. The mechanical interlock between the attachment portion of the goggles and the attachment portion of the helmet may be effectuated by the protrusion of latch member being physically impeded by the protrusion of the latch opening and thereby preventing retraction of the latch member out of the latch opening. All the magnetic attractors may be magnets. The attachment portion of the goggles includes at least one magnetic attractor oriented parallel to the axial length of the latch member and configured to magnetically attract to at least one corresponding and complimentary magnetic attractor of the attachment portion of the helmet.

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112(f). Thus, the use of the words "function," "means" or "step" in the Detailed Description or Description of the Drawings or claims is not intended to somehow indicate a desire to invoke the special provisions of 35 U.S.C. § 112(f), to define the invention. To the contrary, if the provisions of 35 U.S.C. § 112(f) are sought to be invoked to define the inventions, the claims will specifically and expressly state the exact phrases "means for" or "step for", and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . .," if the claims also recite any structure, material or acts in support of that means or step, or that perform the recited function, then it is the clear intention of the inventors not to invoke the provisions of 35 U.S.C. § 112(f). Moreover, even if the provisions of 35 U.S.C. § 112(f) are invoked to define the claimed aspects, it is intended that these aspects not be limited only to the specific structure, material or acts that are described in the preferred embodiments, but in addition, include any and all structures, materials or acts that perform the claimed function as described in alternative embodiments or forms of the disclosure, or that are well known present or later-developed, equivalent structures, material or acts for performing the claimed function.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

The invention will hereinafter be described in conjunction with the appended drawings, where like designations denote like elements, and.

DETAILED DESCRIPTION

This disclosure, its aspects and implementations, are not limited to the specific material types, components, methods, or other examples disclosed herein. Many additional material types, components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

While this disclosure includes a number of embodiments in many different forms, there is shown in the drawings and will herein be described in detail particular embodiments with the understanding that the present disclosure is to be considered as an exemplification of the principles of the disclosed methods and systems, and is not intended to limit the broad aspect of the disclosed concepts to the embodiments illustrated.

Figure 1:
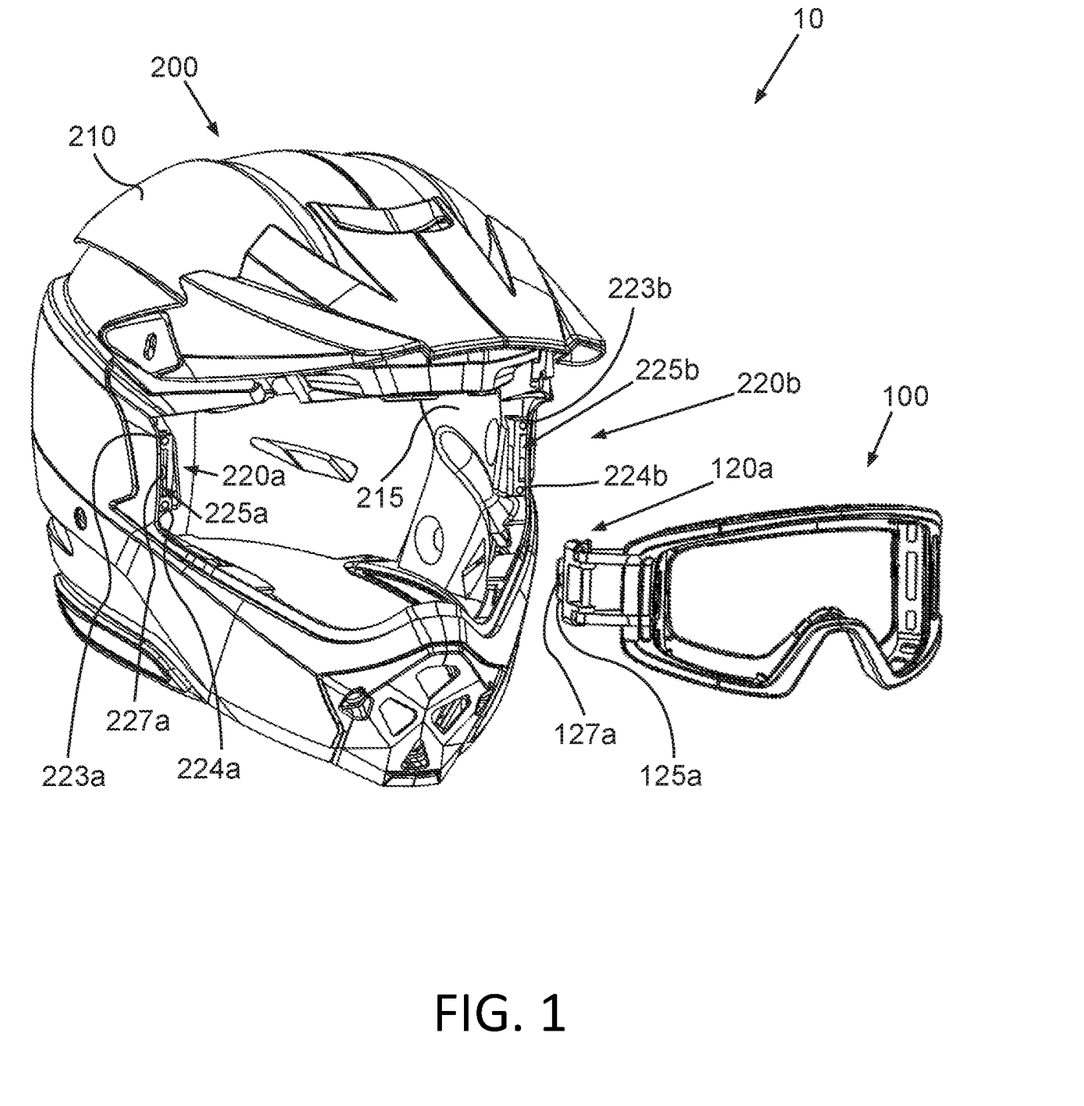
FIG. 1 is a front perspective view of an embodiment of a helmet-goggle attachment system including an embodiment of goggles and an embodiment of a helmet.

A need exists for a secure attachment device that allows users to readily and efficiently put goggles on and take them off while wearing a helmet and ensure that the goggles, when worn, maintain a proper fit. With reference to the drawings, FIG. 1 depicts a front perspective view of an embodiment of helmet-goggle attachment system 10 including an embodiment of goggles 200 and an embodiment of a helmet 100. The goggles 100 may include at least one attachment portion 120, such as a right side goggle attachment portion 120a and a left side goggle attachment portion 120b (not-shown). The right and left side goggle attachment portions 120a-b may be structurally mirrored, so that they include reciprocal features and functionality. For purposes of description presented herein, features generally located on the right side of the helmet-goggle attachment system components may be denoted with a numeral followed by a lower-case "a", while features generally located on the right side of the helmet-goggle attachment system components may be denoted with a numeral followed by a lower-case "b." A goggle attachment portion 120 may be configured to mate with and removably attach to an at least one corresponding and complimentary helmet attachment portion 220, such as a right side helmet attachment portion 220a and a left side helmet attachment portion 220b, each located on an interior surface 215 of the helmet 200, as depicted, inter alia, in FIGS. 1-7. Like the goggle attachment portions 120a-b, the helmet attachment portions 220a-b may be correspondingly and complimentarily mirrored, so that they also include reciprocal features and functionality. The helmet 200 may have an exterior surface 210. The combined structural features and functional operation of a goggle attachment portion 120 with a helmet attachment portion 220 may jointly comprise a magnetic mechanical latching attachment 5, for connecting goggles 100 to a helmet 200. Together, the embodiment of the helmet 100 and the embodiment of the goggles 200 may comprise components of a helmet-goggle attachment system 10.

Referring further to the FIG. 1, each helmet attachment portion 220, such as right and left side helmet attachment portions 220a and 220b, may include one or more magnetic attractors, such as axially-oriented magnetic attractors 223a and 224a and 223b and 224b, respectively. Moreover, each helmet attachment portion 220, such as helmet right and left side helmet attachment portions 220a and 220b, may also include at least one perpendicularly-oriented magnetic attractor 227, such as perpendicularly-oriented magnetic attractors 227a and 227b (not shown). In a like manner, a goggle attachment portion 120, such as right and left side goggle attachment portions 120a and 120b, may include one or more complimentarily-located magnetic attractors, such as perpendicularly-oriented magnetic attractors 127a and 127b (not shown) and/or axially-oriented magnetic attractors 123a and 124a, as well as axially-oriented magnetic attractors 123b and 124b (also not shown). The orientation of various component elements of the helmet-goggle attachment system 10, such as the magnetic attractors 223, 224 and 227, on both the right and left sides of the helmet-goggle attachment system 10, may be defined generally by an axis, such as axis 1 depicted in FIGS. 5 and 6, corresponding to the direction of travel that a goggle attachment portion 120 traverses when it mates with and is removably coupled to, or otherwise releasably attached to, the helmet attachment portion 220. Furthermore, the orientation of various component elements of the helmet-goggle attachment system 10 may additionally be generally defined by another axis, such as axis 2, which is perpendicular to axis 1. The magnetic attractors 123, 124, 127, 223, 224 and 227 may be magnets, or may otherwise compose magnetically attractive functionality. The goggle attachment portion 120 may include a latch member 125, such as right and left latch members 125a and 125b (not shown), wherein the latch member may be configured to mate with a corresponding and complimentary latch opening 225, such as right and left latch openings 225a and 225b, of the helmet attachment portion 220. The helmet attachment portion may be configured to be securely, and yet, removably attached to a surface, such as interior surface 215, of the helmet 200.

Figure 2:
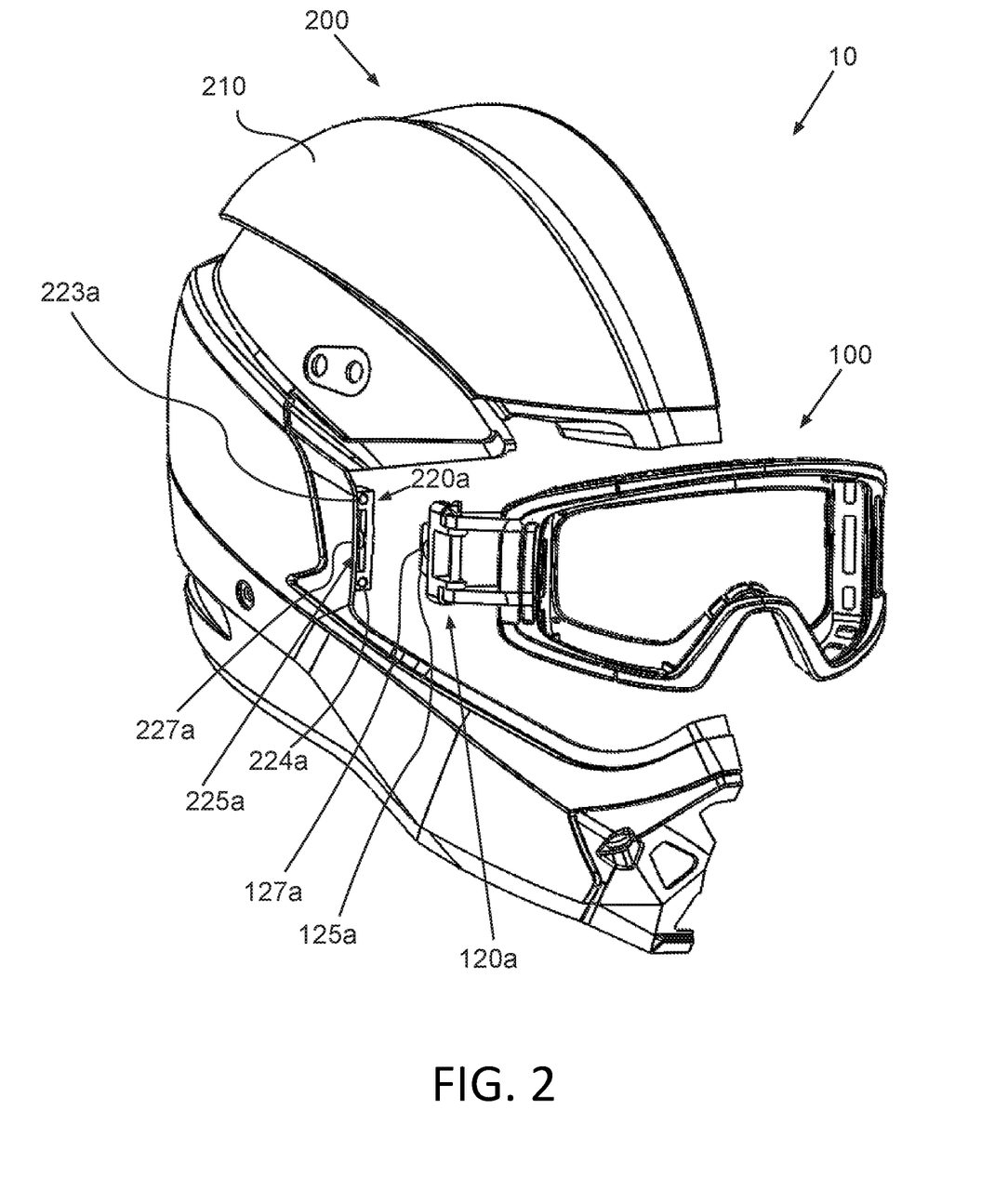
FIG. 2 is a front perspective view of the helmet-goggle attachment system of FIG. 1 just prior to the goggles being coupled to the helmet, wherein a portion of the helmet has been cut-away for clarity.
Figure 3:
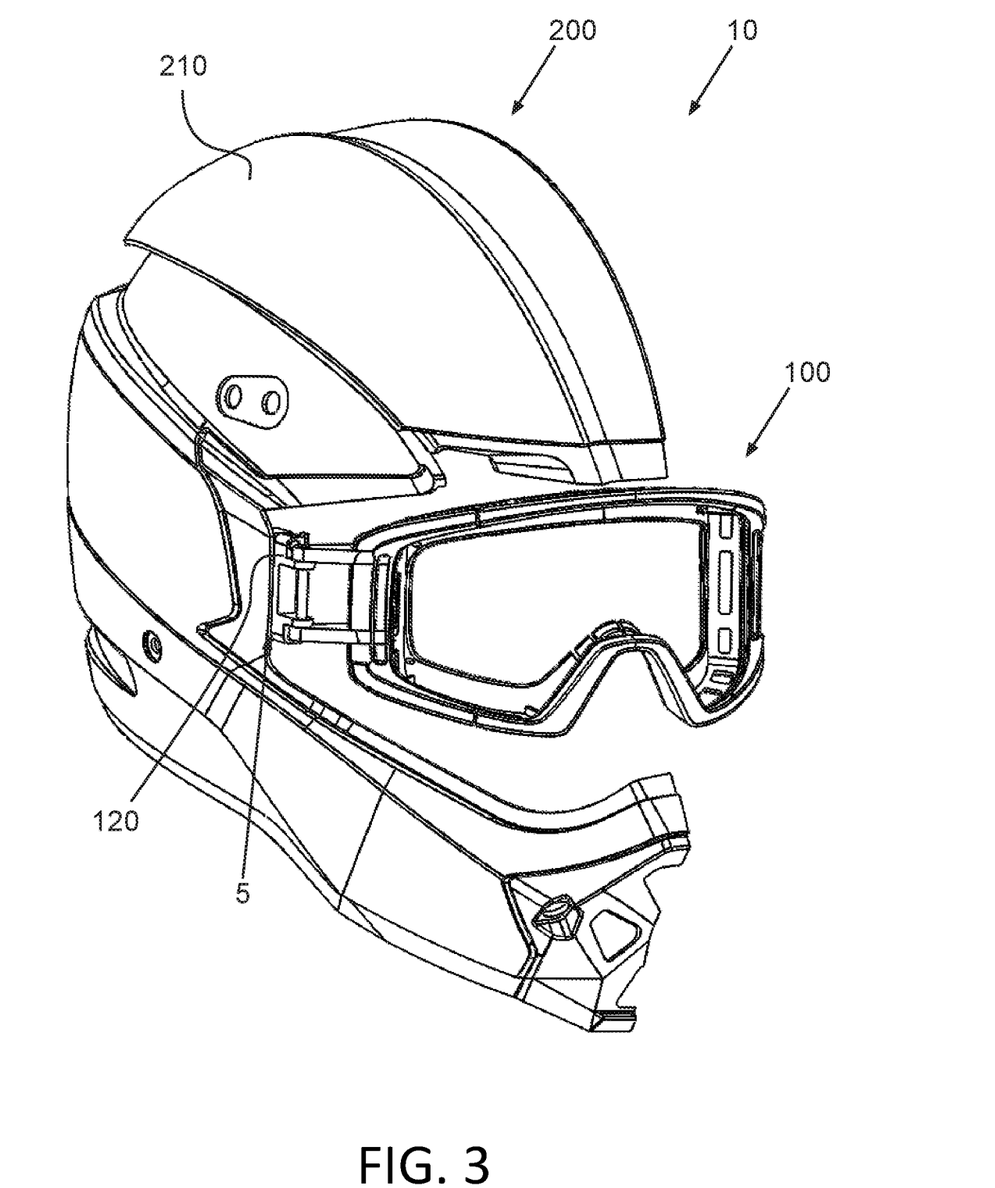
FIG. 3 is a front perspective view of the helmet-goggle attachment system of FIG. 1 with the goggles removably coupled to the helmet, wherein a portion of the helmet has again been cut-away for clarity
Figure 4:
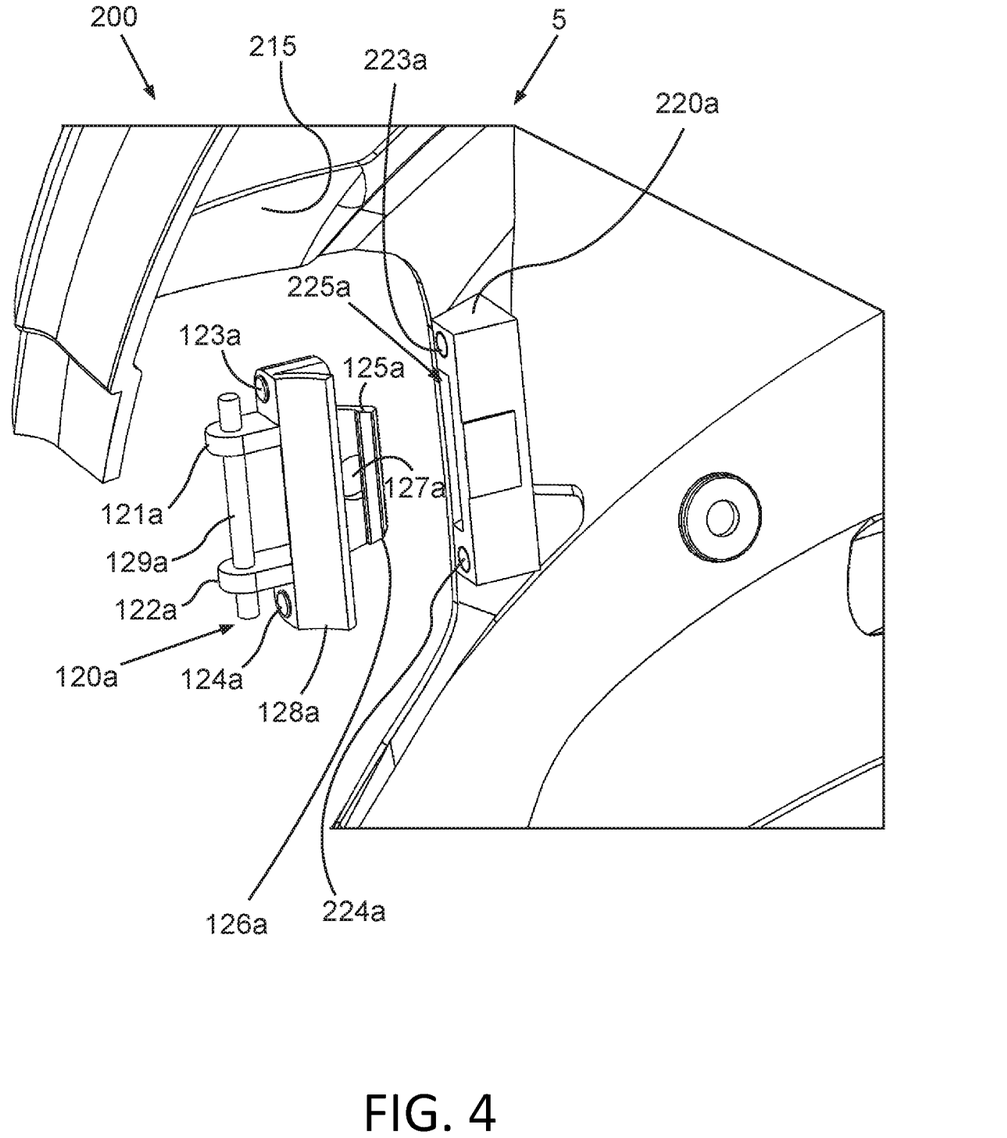
FIG. 4 is a side perspective partial cut-away view of an embodiment of a goggle attachment portion prior to coupling with an embodiment of a helmet attachment portion on an inside surface of an embodiment of a helmet.
Figure 5:
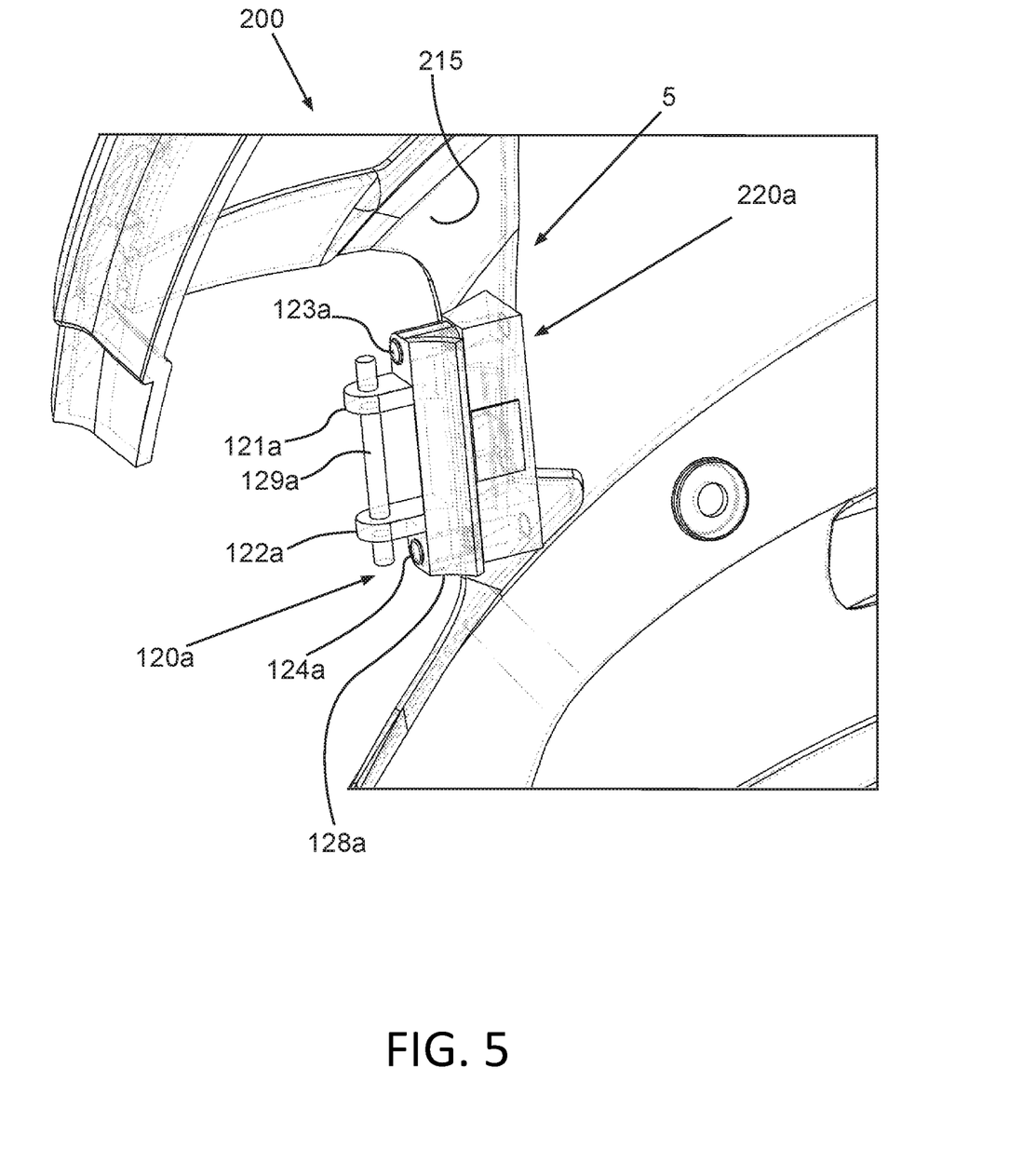
FIG. 5 is a side perspective partial cut-away view of an embodiment of a goggle attachment portion removably coupled with an embodiment of a helmet attachment portion on an inside surface of an embodiment of a helmet.

As further set forth in reference to the drawings, FIG. 4 illustrates a more zoomed in side perspective partial view of a magnetic mechanical latching attachment 5, prior to operable coupling of a goggle attachment portion 120a with a corresponding and complimentary helmet attachment portion 220 located on the right inside surface 215 of helmet 200. With the goggles 100 removed from the view, the magnetic attractors 123a and 124a of the goggle attachment portion 120a are clearly visible. In addition, spacer posts 121a and 122a, along with attachment support rod 129a, of the goggle attachment portion 120a are also clearly visible. Goggles 100 may be configured to operate with goggle attachment portion 120a. The goggle attachment portion 120a may be configured to be securely, and yet, removably attached to goggles 100 by engaging spacer posts 121a and 122a, along with attachment support rod 129a, of the goggle attachment portion 120a as shown in FIGS. 1, 2 and 3. A protrusion 126a, such as a lip, ridge, or other like feature, may be formed onto and protrude from the latch member 125a of the goggle attachment portion 120a. Embodiments of a goggle attachment portion may include a detachment actuation member 128a. The detachment actuation member 128a may be configured so that a user of the magnetic mechanical latching attachment 5 may utilize the detachment actuation member 128a to apply a force to the goggle attachment portion 120a and actuate detachment, uncoupling, or otherwise remove the goggle attachment portion 120a from a mated condition with the helmet attachment portion 220a, as shown in FIG. 5. The application of a force upon the detachment actuation member 128a may be applied by a user's fingers and may be readily effected by engagement of the user's fingers with the detachment actuation member 128a whether or not the user is wearing gloves. The location of the helmet attachment portion 220a on the interior surface 215 of the helmet 200 may provide advantage access to the magnetic mechanical latch attachment 5 and may help shield the attachment 5 from decoupling due to engagement with environmental elements. Thus, a helmet-goggle attachment system 10 may be utilized in various environmental conditions and operate with various helmet 200 and goggle 100 designs.

As further set forth in reference to the drawings, FIG. 4 illustrates a more zoomed in side perspective partial view of a magnetic mechanical latching attachment 5, prior to operable coupling of a goggle attachment portion 120a with a corresponding and complimentary helmet attachment portion 220 located on the right inside surface 215 of helmet 200. With the goggles 100 removed from the view, the magnetic attractors 123a and 124a of the goggle attachment portion 120a are clearly visible. In addition, spacer posts 121a and 122a, along with attachment support rod 129a, of the goggle attachment portion 120a are also clearly visible. Goggles 100 may be configured to operate with goggle attachment portion 120a. The goggle attachment portion 120a may be configured to be securely, and yet, removably attached to goggles 100. A protrusion 126a, such as a lip, ridge, or other like feature, may be formed onto and protrude from the latch member 125a of the goggle attachment portion 120a. Embodiments of a goggle attachment portion may include a detachment actuation member 128a. The detachment actuation member 128a may be configured so that a user of the magnetic mechanical latching attachment 5 may utilize the detachment actuation member 128a to apply a force to the goggle attachment portion 120a and actuate detachment, uncoupling, or otherwise remove the goggle attachment portion 120a from a mated condition with the helmet attachment portion 220a, as shown in FIG. 5. The application of a force upon the detachment actuation member 128a may be applied by a user's fingers and may be readily effected by engagement of the user's fingers with the detachment actuation member 128a whether or not the user is wearing gloves. The location of the helmet attachment portion 220a on the interior surface 215 of the helmet 200 may provide advantage access to the magnetic mechanical latch attachment 5 and may help shield the attachment 5 from decoupling due to engagement with environmental elements. Thus, a helmet-goggle attachment system 10 may be utilized in various environmental conditions and operate with various helmet 200 and goggle 100 designs.

Figure 6:
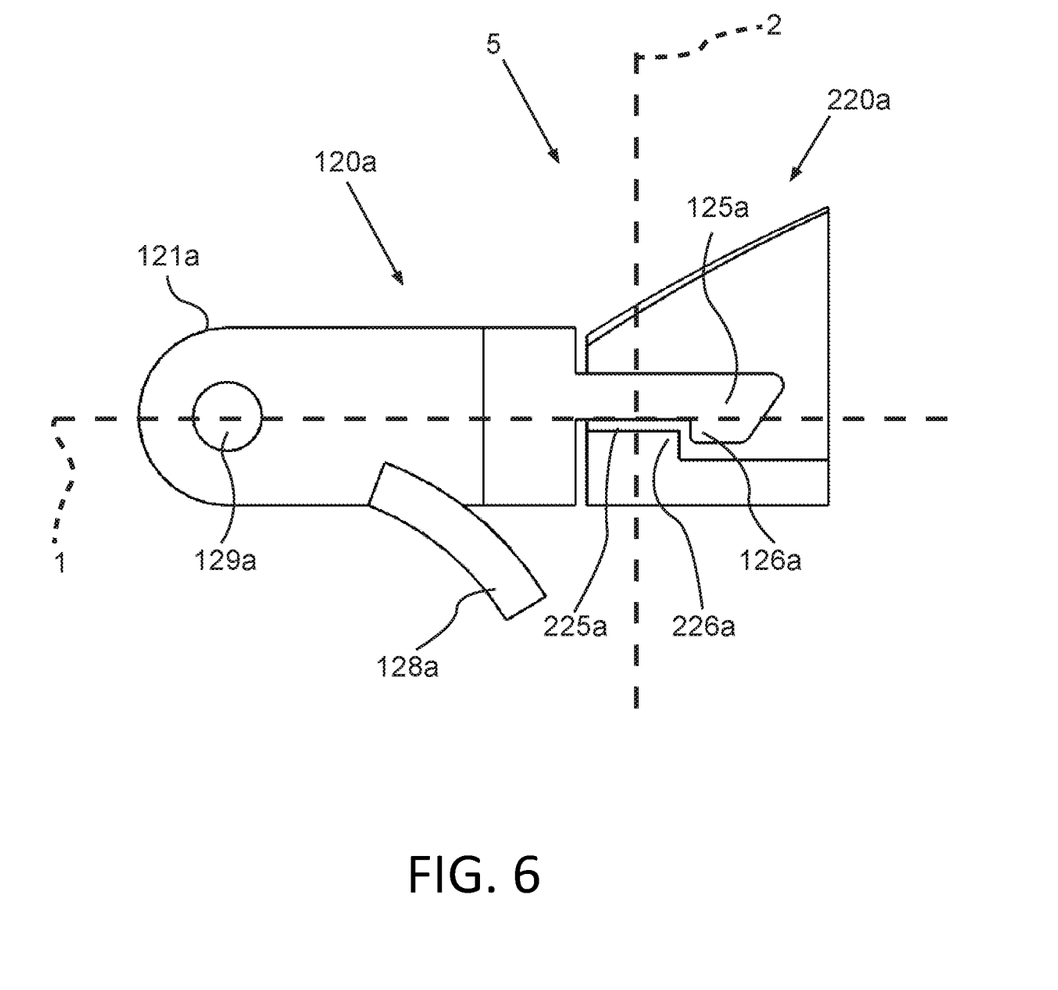
FIG. 6 is a side cut-away view of an embodiment of a goggle attachment portion coupled to an embodiment of a helmet attachment portion.
Figure 7:
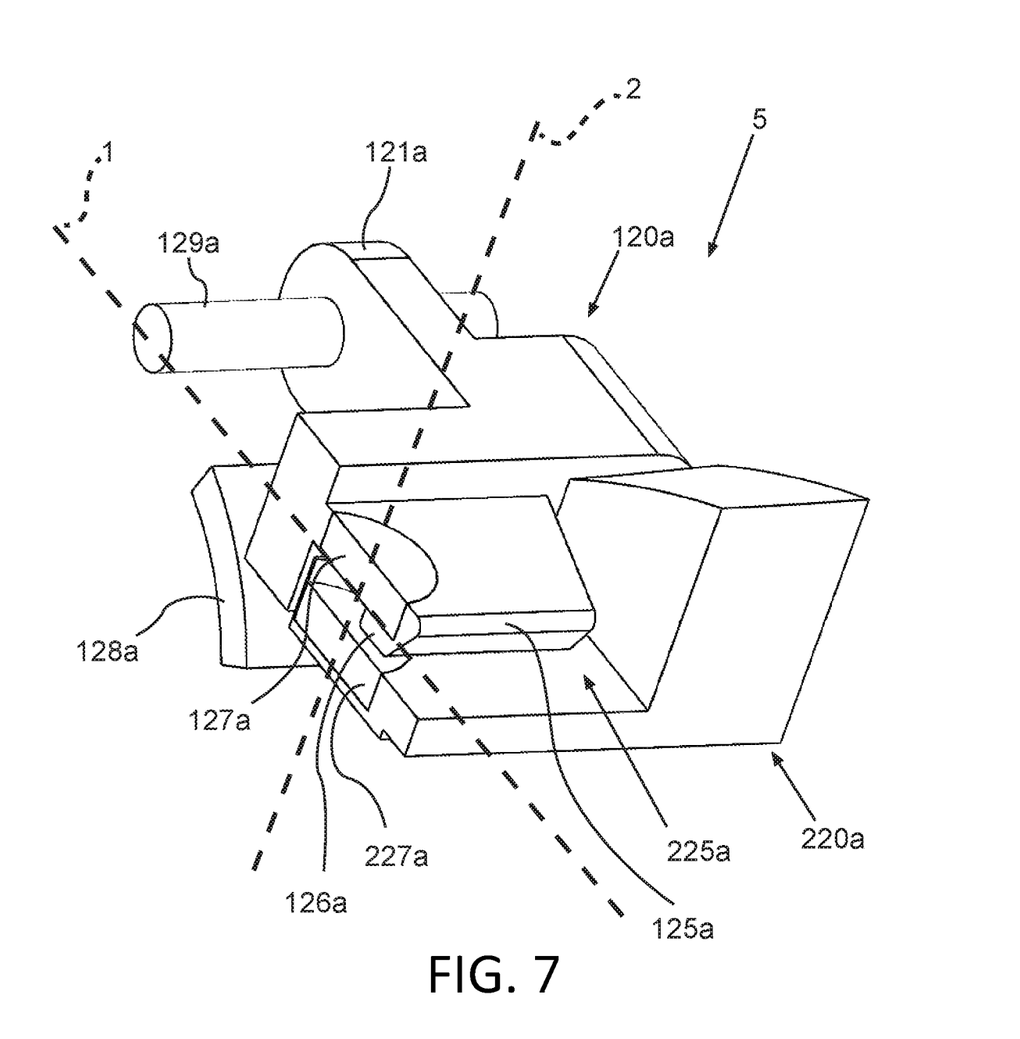
FIG. 7 is a side perspective cut-away view of an embodiment of a goggle attachment portion coupled to an embodiment of a helmet attachment portion.

Referring still further to the drawings, FIG. 6 depicts a side cut-away view of an embodiment of a google attachment portion 120a coupled to an embodiment of a helmet attachment portion 220a. The mechanical latch member 125a may include a latch protrusion 126a extending perpendicular to an axial length of the latch member 125a. The axial length of the latch member 125a may correspond with and/or run parallel to axis 1. The perpendicular expansion of the protrusion 126a may correspond with and/or run parallel to axis 2. Likewise, the latch opening 225a of the helmet attachment portion 220a may include protrusion 226a extending perpendicular to an axial length of the latch opening 225a. In a similar manner, the perpendicular expansion of the protrusion 226a may also correspond with and/or run parallel to axis 2. When the goggle attachment portion 120a is mated with the helmet attachment portion 220a, so that the latch member 125a of the goggle attachment portion 120a is inserted into the latch opening 225a of the helmet attachment portion 220a, the perpendicularly-oriented protrusions 126a and 226a may form or otherwise help facilitate a mechanical interlock between the attachment portion 120a of the goggles and the attachment portion 220a of the helmet. To disengage the mechanical interlock, a user may apply a force to the detachment actuation member causing the protrusion 126a of the latch member 125a to slip or otherwise move perpendicularly away from and past the protrusion 226a of the latch opening 225a, thereby permitting an axial retractions of the latch member 125a of the goggle attachment portion 120a from out of the latch opening 225a of the helmet attachment portion 220a With continued reference to the drawings, FIG. 7 depicts a side perspective cut-away view of an embodiment of a google attachment portion 120a removably coupled to an embodiment of a helmet attachment portion 220a. It is understood that removably coupled means once a goggle attachment portion 120a is coupled to, or otherwise mated with and attached to a helmet attachment portion 220a, the two component may be thereafter uncoupled, disconnected, unattached or otherwise removed from each other and maneuvered to an un-mated condition. As shown, the magnetic attractor, such as the perpendicularly-oriented magnetic attractor 127a, of the attachment portion 120a of the goggles 100 may be magnetically attracted to the magnetic attractor, such as magnetic attractor 227a, of the attachment portion 220 of the helmet 200. When in a mated condition, the magnetic attraction between the magnetic attractor 127a and the magnetic attractor 227a may present a force that may help further facilitate the mechanical interlock between the protrusion 126a from the latching member 125a of the attachment portion 120a of the goggles 100 and the protrusion 226a from the latch opening 225a of the attachment portion 220a of the helmet 200. Moreover, the magnetic attraction of the perpendicularly-oriented magnetic attractors 123a and/or 124a of the goggle attachment portion 120a to the perpendicularly-oriented magnetic attractors 223a and/or 224a of the helmet portion may facilitate a holding of the mechanical latch member 125a of the goggle attachment portion 120a in a locked position with respect to the latch opening 225a of the helmet attachment portion 220a in a manner wherein axial movement of the goggle attachment portion 120a away from the helmet attachment portion 220a is restricted by a mechanical interlock of the perpendicular protrusion 126a of the latch member 125a of the goggle attachment portion 120a with the perpendicular protrusion 226a of the latch opening 225a of the helmet attachment portion 220a.

Methodology pertaining to the functionality and operation of a magnetic mechanical latch attachment 5, in conjunction with a helmet-goggle attachment system 10, may include coupling goggles 100 to a helmet. The coupling of the goggles 100 to the helmet 200 may include the provision of goggles 100 having a latch member, such as latch member 125a. The coupling of the goggles 100 to the helmet 200 may further include the provision of a helmet 200 having a latch opening, such as latch opening 225a, positioned on an interior surface 215 of the helmet 200. In addition, the latch opening 225a may be configured to receive and removably latch to the latch member 125a of the goggles 100. Furthermore, the coupling the goggles 100 to the helmet 200 may include removably latching the latch member 125a of the goggles 100 to the latch opening 225a located on the interior surface 215 of the helmet 200.

Where the above examples, embodiments and implementations reference examples, it should be understood by those of ordinary skill in the art that other helmets and manufacturing methods and examples could be intermixed or substituted with those provided. In places where the description above refers to particular embodiments of helmets, hoses, coupling segments and customization methods, it should be readily apparent that a number of modifications may be made without departing from the spirit thereof and that these embodiments and implementations may be applied to other to helmet assembly methods as well. Accordingly, the disclosed subject matter is intended to embrace all such alterations, modifications and variations that fall within the spirit and scope of the disclosure and the knowledge of one of ordinary skill in the art.

What is claimed is:

1. A magnetic mechanical latching attachment for connecting goggles to a helmet, the magnetic mechanical latching attachment comprising:
   a goggle attachment portion having at least one axially-oriented magnetic attractor and a mechanical latch member, the mechanical latch member including:
   a latch protrusion extending perpendicular to an axial length of the latch member, and optionally at least one perpendicularly-oriented magnetic attractor,
   wherein the goggle attachment portion is configured to attach to goggles;
   a helmet attachment portion having at least one axially-oriented magnetic attractor and a latch opening, the latch opening including
   a latch protrusion extending perpendicular to an axial length of the latch opening, and optionally at least one perpendicularly-oriented magnetic attractor,
   wherein the helmet attachment portion is attached to a surface of a helmet; and
   wherein the latch member of the goggle attachment portion is configured to mate with the latch opening of the helmet attachment portion, and, when mated, the at least one axially-oriented magnetic attractor of the goggle attachment portion is located such that it is magnetically attracted to the at least one axially-oriented magnetic attractor of the helmet portion, wherein the magnetic attraction of the axially-oriented magnetic attractor of the goggle attachment portion to the axially-oriented magnetic attractor of the helmet portion facilitates a holding of the mechanical latch member of the goggle attachment portion in a locked position with respect to the latch opening of the helmet attachment portion in a manner wherein axial movement of the goggle attachment portion away from the helmet attachment portion is restricted by a mechanical interlock of the perpendicular protrusion of the latch member of the goggle attachment portion with the perpendicular protrusion of the latch opening of the helmet attachment portion.

2. The magnetic mechanical latching attachment of claim 1, wherein the helmet attachment portion is located on an interior surface of the helmet.

3. The magnetic mechanical latching attachment of claim 1, wherein the at least one perpendicularly-oriented magnetic attractor of the mechanical latch member of the goggle attachment portion when present, the at least one perpendicularly-oriented magnetic attractor of the latch opening of the helmet attachment portion when present, the at least one axially-oriented magnetic attractor of the goggle attachment portion, and the at least one axially-oriented magnetic attractor of the helmet attachment portion all include magnets.

4. The magnetic mechanical latching attachment of claim 1, wherein the goggle attachment portion further comprises at least one perpendicularly-oriented magnetic attractor and the helmet attachment portion further comprises at least one perpendicularly-oriented magnetic attractor.

5. The magnetic mechanical latching attachment of claim 1,
   wherein, when the goggle attachment portion is mated with the helmet attachment portions, the at least one axially-oriented magnetic attractor of the goggle attachment portion is located such that it is magnetically attracted to the at least one axially-oriented magnetic attractor of the helmet portion.

6. The magnetic mechanical latching attachment of claim 5, wherein the magnetic attraction between the axially-oriented magnetic attractor of the goggle attachment portion and the axially-oriented magnetic attractor of the helmet attachment portion tends the goggle attachment portion towards a mated condition with the helmet attachment portion.

7. The magnetic mechanical latching attachment of claim 1, wherein the goggle attachment portion is configured to be securely and removably attached to goggles.

\* \* \* \* \*